United States Patent [19]

Chandraratna et al.

[11] Patent Number: 5,451,605
[45] Date of Patent: Sep. 19, 1995

[54] 1,2-EPOXYCYCLOHEXANYL AND BICYCLIC AROMATIC SUBSTITUTED ETHYNE COMPOUNDS HAVING RETINOID-LIKE BIOLOGICAL ACTIVITY

[75] Inventors: Roshantha A. Chandraratna, Mission Viejo; Richard L. Beard, Santa Ana Heights, both of Calif.

[73] Assignee: Allergan, Inc., Irvine, Calif.

[21] Appl. No.: 177,621

[22] Filed: Dec. 30, 1993

[51] Int. Cl.$^6$ .............. C07D 303/12; C07D 303/17; A01K 31/235; A01K 31/335
[52] U.S. Cl. .................... 514/475; 514/314; 514/415; 514/443; 514/469; 546/152; 546/160; 546/169; 546/174; 546/175; 546/180; 548/494; 548/503; 548/504; 548/507; 548/509; 549/57; 549/58; 549/429; 549/467; 549/408; 549/470; 549/471; 549/546
[58] Field of Search .............. 549/546, 57, 58, 429, 549/467, 468, 470, 471; 514/314, 415, 443, 469, 475; 546/160, 169, 174, 175, 180, 152; 548/494, 503, 504, 507, 509

[56] References Cited

U.S. PATENT DOCUMENTS

| 3,347,875 | 10/1967 | Foster et al. | 549/546 |
| 4,096,341 | 6/1978 | Frazer . | |
| 4,264,467 | 4/1981 | Schulte-Elte et al. | 549/546 |
| 4,326,055 | 4/1982 | Loeliger . | |

(List continued on next page.)

FOREIGN PATENT DOCUMENTS

| 0130795 | 1/1985 | European Pat. Off. | C07D 311/58 |
| 176034A | 4/1986 | European Pat. Off. | C07C 63/66 |
| 0272921 | 6/1988 | European Pat. Off. | C07D 213/80 |
| 0284288 | 9/1988 | European Pat. Off. | C07D 401/04 |
| 0350846 | 7/1989 | European Pat. Off. | C07D 311/58 |
| 3708060 | 9/1987 | Germany | C07D 311/04 |

OTHER PUBLICATIONS

A General Synthesis of Terminal and Internal Arylalkynes by the Palladium-Catalyzed Reaction of Alkynylzinc Reagents with Aryl Halides by Anthony O. King and Ei-ichi Negishi, *J. Org. Chem.* 43 No. 2, 1978 p. 358.

(List continued on next page.)

Primary Examiner—Joseph E. Evans
Attorney, Agent, or Firm—Gabor L. Szekeres; Robert J. Baran; Martin A. Voet

[57] ABSTRACT

Compounds of the formula

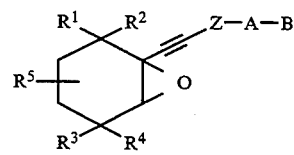

where $R_1$–$R_5$ are hydrogen, lower alkyl of 1–6 carbons, or halogen; A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds; B is hydrogen, COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, and Z is

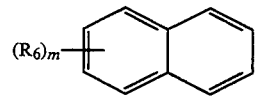

wherein $R_6$ is hydrogen, lower alkyl of 1–6 carbons, or halogen, $R_6$ can be attached to any available position on the Z group, and m is an integer between 0 to 4, have retinoid-like biological activity.

19 Claims, No Drawings

U.S. PATENT DOCUMENTS

| | | | |
|---|---|---|---|
| 4,391,731 | 7/1983 | Boller et al. | 252/299.62 |
| 4,695,649 | 9/1987 | Magami et al. | |
| 4,723,028 | 2/1988 | Shudo | |
| 4,739,098 | 4/1988 | Chandraratna | |
| 4,740,519 | 4/1988 | Shroot et al. | |
| 4,749,715 | 6/1988 | Hall | 514/469 |
| 4,810,804 | 3/1989 | Chandraratna | |
| 4,826,969 | 5/1989 | Maignan et al. | |
| 4,855,320 | 8/1989 | Chatterjee et al. | |
| 4,895,868 | 1/1990 | Chandraratna | |
| 4,927,947 | 5/1990 | Chandraratna | 549/484 |
| 4,980,369 | 12/1990 | Chandraratna | |
| 4,981,981 | 1/1991 | Aldrich et al. | 549/546 |
| 4,992,468 | 2/1991 | Chandraratna | |
| 5,006,550 | 4/1991 | Chandraratna | |
| 5,013,744 | 5/1991 | Chandraratna | |
| 5,015,658 | 5/1991 | Chandraratna | |
| 5,023,341 | 6/1991 | Chandraratna | |
| 5,037,825 | 8/1991 | Klaus et al. | 514/233.8 |
| 5,045,551 | 9/1991 | Chandraratna | |
| 5,053,523 | 10/1991 | Chandraratna | |
| 5,068,252 | 11/1991 | Chandraratna | |
| 5,089,509 | 2/1992 | Chandraratna | |
| 5,130,335 | 7/1992 | Chandraratna | |
| 5,134,159 | 7/1992 | Chandraratna | |
| 5,162,546 | 11/1992 | Chandraratna | 549/23 |
| 5,175,185 | 12/1992 | Chandraratna | 514/445 |
| 5,183,827 | 2/1993 | Chandraratna | 514/444 |
| 5,202,471 | 4/1993 | Chandraratna | 562/473 |
| 5,231,113 | 7/1993 | Chandraratna | 514/510 |
| 5,234,926 | 8/1993 | Chandraratna | 514/253 |
| 5,248,777 | 9/1993 | Chandraratna | 546/165 |
| 5,264,456 | 11/1993 | Chandraratna | 514/461 |
| 5,264,578 | 11/1993 | Chandraratna | 546/269 |
| 5,272,156 | 12/1993 | Chandraratna | 514/314 |
| 5,278,318 | 1/1994 | Chandraratna | 549/23 |

OTHER PUBLICATIONS

Conversion of Methyl Ketones into Terminal Acetylenes and (E)-Tri-substituted Olefins of Terpenoid Origin by Ei-ichi, Anthony O. King, and William L. Klima, *J. Org. Chem.* 45 No. 12, 1980 p. 2526.

Sporn et. al. in *J. Amer. Acad. Derm.* 15:756-764 (1986).

A Convenient Synthesis of Ethynlarenes and Diethynylarenes by S. Takahashi, Y. Kuroyama, K. Sonogashira, N. Hagihara, *Synthesis* 1980 p. 627-630.

Shudo et al. in *Chem. Phar. Bull.* 33:404-407 (1985).

Kagechika et. al. in *J. Med. Chem.* 31:2182-2192 (1988).

Chemistry and Biology of Synthetic Retinoids by Marcia I. Dawson and William H. Okamura, published by CRC Press Inc., 1990, pp. 334-335, 354.

Synthesis of 2,2'-Diacyl-1,1'-biaryls. Regiocontrolled Protection of... by Mervic, et al, *J. Org. Chem.*, No. 45, pp. 4720-4725, 1980.

A Dopamine Receptor Model and Its Application in the Design of a New Class of Rigid Pyrrolo[2,3-g]isoquinoline Antipsychotics, Gary L. Olson, et al. *American Chemical Society,* 1981, vol. 24, No. 9, pp. 1026-1031.

6.2.3 Conformational Restriction, Williams, et al., *Drug Discovery and Development,* 1987 The Human Press, pp. 54-55.

V. Retinoid Structure-Biological Activiey Relationships, Chemistry and Biology of Synthetic Retinoids, pp. 324-356 (1990).

Davis et al. *J. Organomettalic Chem* 387 (1990) 381-390.

Effects of 13-Cis-Retinoic Acid, All-Trans-Retinoic Acid, and Acitretion on the Proliferation, Lipid Synthesis and Keratin Expression of Cultured Human Sebocytes In Vitro, C. C. Zouboulis, *The Journal of Investigative Dermatology,* vol. 96, No. 5, May 1991, pp. 792-797.

Organ maintenance of human sebaceous glands: in vitro effects of 13-cis retinoic acid and testosterone, John Ridden, et al., Journal of Cell *Science,* vol. 95, 1990, pp. 125-136.

Characterization of Human Sebaceous Cells In Vitro, Thomas I. Doran, et al., *The Journal of Investigative Dermatology,* vol. 96, No. 3, Mar. 1991.

1,2-EPOXYCYCLOHEXANYL AND BICYCLIC AROMATIC SUBSTITUTED ETHYNE COMPOUNDS HAVING RETINOID-LIKE BIOLOGICAL ACTIVITY

FIELD OF THE INVENTION

The present invention is directed to novel compounds which have retinoid-like biological activity. More specifically, the present invention relates to ethyne compounds which have a substituted 1,2-epoxycyclohexanyl and a substituted bicyclic aromatic substituent. The bicyclic aromatic group may have an acid or ester function, which may also be converted to an alcohol, aldehyde or ketone, or derivatives thereof, or may be reduced to —$CH_3$.

RELATED ART

Compounds which have retinoid like activity are well known in the art, and are described in numerous United States and foreign patents and in scientific publications. It is generally known and accepted in the art that retinoid like activity is useful for treating animals of the mammalian species, including humans, for curing or alleviating the symptoms and conditions of numerous diseases and conditions. In other words, it is generally accepted in the art that pharmaceutical compositions having a retinoid like compound or compounds as the active ingredient are useful as regulators of cell proliferation and differentiation, and particularly as agents for treating dermatoses, such as acne, Darier's disease, psoriasis, icthyosis, eczema and atopic dermatitis, and for treating and preventing malignant hyperproliferative diseases such as epithelial cancer, breast cancer, prostatic cancer, head and neck cancer and myeloid leukemias, for reversing and preventing atherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus) for treating chronic inflammatory diseases such as pulmonary fibrosis, for treating and preventing diseases associated with lipid metabolism and transport such as dyslipidemias, for promoting wound healing, for treating dry eye syndrome and for reversing and preventing the effects of sun damage to skin.

U.S. Pat. No. 4,739,098 describes but-3-en-1-ynyl compounds which are substituted in the 1-position by an aromatic acid or ester, and on the 4-position by an alkyl-substituted -1-cyclohexene moiety. U.S. Pat. No. 4,927,947 describes but-3-en-1-ynyl compounds which are substituted in the 1-position by a heteroaromatic acid or ester, and on the 4-position by an alkyl-substituted -1-cyclohexene moiety.

U.S. Pat. Nos. 4,980,369, 5,013,744, 5,023,341, 5,045,551, 5,053,523, 5,089,509, and 5,162,546 describe ethyne compounds substituted with a heteroaromatic or monocyclic aromatic substituent and also with a second monocyclic aromatic or heteroaromatic substituent. The compounds described in these patents have retinoid-like biological activity.

SUMMARY OF INVENTION

The present invention relates to compounds of Formula 1

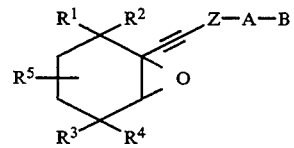

where $R_1$–$R_5$ are hydrogen, lower alkyl of 1–6 carbons, or halogen;

A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, and Z is selected from a bivalent radical derived from the groups:

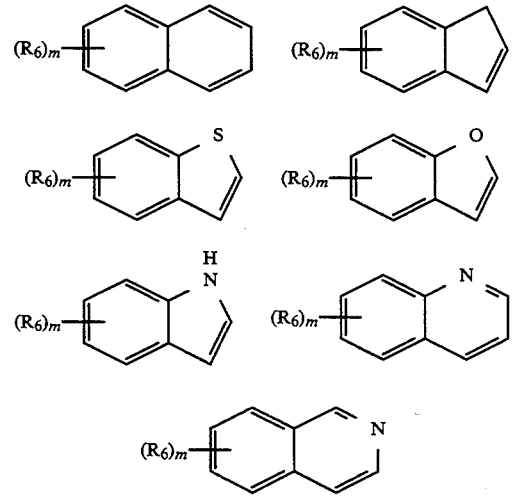

wherein $R_6$ is hydrogen, lower alkyl of 1–6 carbons, or halogen, $R_6$ can be attached to any available position on the Z group, and m is an integer between 0 to 4.

In a second aspect, this invention relates to the use of the compounds of Formula 1 as regulators for cell proliferation and differentiation, and particularly as agents for treating dermatoses, such as acne, Darier's disease, psoriasis, icthyosis, eczema, atopic dermatitis, and for treating and preventing malignant hyperproliferative diseases such as epithelial cancer, breast cancer, prostatic cancer, head and neck cancer and myeloid leukemias, for reversing and preventing artherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus), for treating chronic inflammatory diseases such as pulmonary fibrosis, for treating and preventing diseases associated with lipid metabolism and transport such as dyslipidemias, for promoting wound healing, for treating dry eye syndrome and in reversing and preventing the effects of sun damage to skin.

This invention also relates to a pharmaceutical composition comprising a compound of Formula 1 in admixture with a pharmaceutically acceptable excipient.

In another aspect, this invention relates to the process for making a compound of Formula 1, which process comprises reacting a compound of Formula 2, where the symbols $R_1$–$R_5$, Z, A and B are defined as above, with an epoxidizing agent, converting the ester of Formula 1 to an acid; and to prepare compounds in which A is $(CH_2)_n$ and n is 1–5, homologating a compound of Formula 1 to increase the value of n, or converting an acid of Formula 1 to an ester; or converting an acid of Formula 1 to an amide; or reducing and acid of Formula 1 to an alcohol of aldehyde; or converting an alcohol of Formula 1 to an ether or ester; or converting an aldehyde of Formula 1 to an acetal.

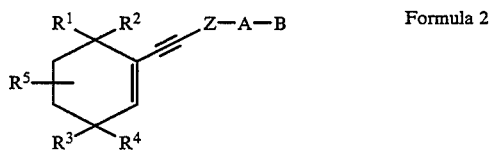

Formula 2

DETAILED DESCRIPTION OF THE INVENTION

General Embodiments

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Lower alkyl means the above-defined broad definition of alkyl groups having 1 to 6 carbons, and as applicable, 3 to 6 carbons for branch chained and cycloalkyl groups. Lower alkenyl is defined similarly having 2 to 6 carbons for normal alkenyl, and 3 to 6 carbons for branch chained and cycloalkenyl groups.

The term "ester" as used here refers to and covers any compound falling within the definition of that term as classically used in organic chemistry. It includes organic and inorganic esters. Where B (of Formula 1) is —COOH, this term covers the products derived from treatment of this function with alcohols or thioalcohols preferably with aliphatic alcohols having 1–6 carbons. Where the ester is derived from compounds where B is —CH$_2$OH, this term covers compounds derived from organic acids capable of forming esters including phosphorous based and sulfur based acids, or compounds of the formula —CH$_2$OCOR$_{11}$ where R$_{11}$ is defined as above.

The term "amides" has the meaning classically accorded that term in organic chemistry. In this instance it includes the unsubstituted amides and all aliphatic and aromatic mono- and di-substituted amides.

A pharmaceutically acceptable salt may be prepared for any compounds in this invention having a functionality capable of forming such-salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The compounds of the present invention may contain one or more double bonds and therefore may have trans and cis (E and Z) isomers. In adddition, the compounds of the present invention contain two or more chiral centers and therefore exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well.

The preferred compounds of this invention are those of Formula 1 where the Z group is naphthalene, benzothiophene or benzofuran. Regarding the A-B group, compounds are preferred where A is $(CH_2)_n$ and n is 0, 1, or 2; and B is —COOH, an alkali metal salt or organic amine salt thereof. Alternatively, compounds are preferred where B is represented by COOR$_8$ (ester) where R$_8$ is lower alkyl, CONR$_9$R$_{10}$ where R$_9$ and R$_{10}$ are hydrogen or lower alkyl (amide), CH$_2$OH (alcohol), CH$_2$OCOR$_{11}$, CH$_2$OR$_{11}$ where R$_{11}$ is lower alkyl; (lower alkyl esters and ethers formed with lower alkanol). Generally speaking, the carboxylic acids esters and amides (B=COOH, COOR$_8$ or CONR$_9$R$_{10}$) are more preferred than the alcohol or its esters (B=CH$_2$OH or CH$_2$OCOR$_{11}$). When the Z group is naphthalene, compounds are preferred where the ethyne group is attached to the 6 position, and the A-B group is attched to the 2 position of the naphthalene ring.

With respect to the substituents on the epoxidized cyclohexane ring, compounds are preferred where R$_1$–R$_5$ are hydrogen or methyl. Still more preferred are compounds where R$_1$ and R$_2$ are methyl and R$_3$ and R$_4$ are hydrogen.

The most preferred compounds of the invention are shown by Formula 3 where:

R$_8$ is hydrogen; 6-[2-(1,2-epoxy-2,6,6-trimethyl-cyclohexan-1-yl)-ethynyl]-2-naphthoic acid, (Compound 1);

R$_8$ is ethyl; ethyl 6-[2-(1,2-epoxy-2,6,6-trimethyl-cyclohexan-1-yl)-ethynyl]-2-naphthoate (Compound 2).

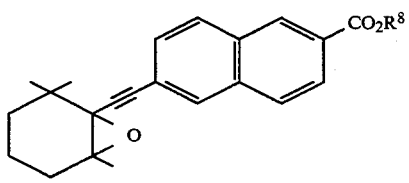

Formula 3

The compounds of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoid-like compounds will be effected by administration of the therapeutically effective dose of one or more compounds of the instant invention. A therapeutic concentration will be that concentration which effects reduction of the particular condition, or retards it expansion. In certain instances, the compound potentially may be used in prophylactic manner to prevent onset of a particular condition. A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg per day of body weight would be expected to effect a therapeutic result in the treatment of many diseases for which these compounds are useful.

The retinoid-like activity of these compounds is confirmed through the classic measure of retinoic acid activity involving the effects of retinoic acid on ornithine decarboxylase. The original work on the correlation between retinoic acid and decrease in cell proliferation was done by Verma & Boutwell, Cancer Research, 1977, 37,2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all causes for ODC activity increases are unknown, it is known that 12-0-tetradecanoylphorbol-13-acetate (TPA) induces ODC activity. Retinoic acid inhibits this induction of ODC activity by TPA. An assay essentially following the procedure set out in Cancer Res: 1662–1670,1975 may be used to demonstrate inhibition of TPA induction of ODC by compounds of this invention. The result of this assay for Compound 1 of this invention is shown in Table 1 below.

TABLE 1

| Compound # | $IC_{80}$ (nmol) |
|---|---|
| 1 | 30.5 |

Synthetic Processes for Preparing Compounds of the Invention

The compounds of this invention can be made by the synthetic chemical pathways illustrated here. The synthetic chemist will readily appreciate that the conditions set out here are specific embodiments which can be generalized to any and all of the compounds represented by Formula 1.

Reaction Scheme 1

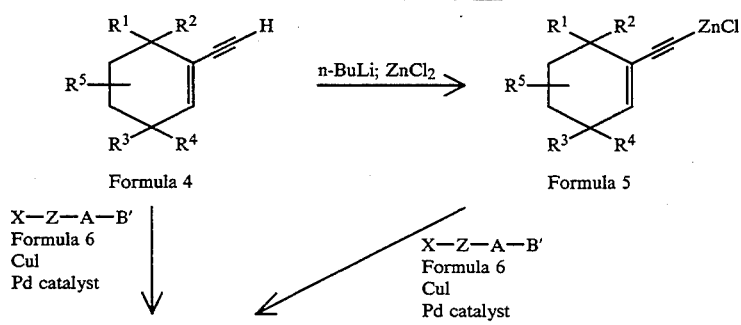

Reaction Scheme 1

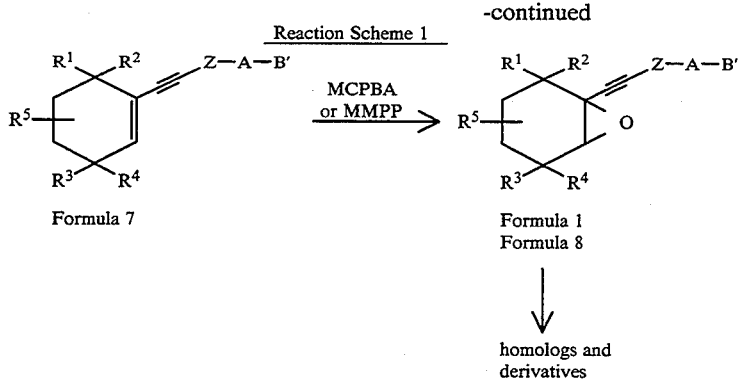

Formula 7          Formula 1
                        Formula 8

↓ homologs and derivatives

In accordance with Reaction Scheme 1 a cyclohexen-1-yl ethyne derivative of Formula 4 is converted into a metal salt, such as a zinc salt of Formula 5. The cyclohexen-1-yl ethyne derivative is obtained in accordance with synthetic processes known in the art (see G. Kobrich et al., Chemische Berichte 1966, 99,689) and already has the desired $R_1$-$R_5$ substituents. For the synthesis of the compounds most preferred in the present invention, the starting compound of Formula 4 is 1,3,3-trimethyl-2-ethynylcyclohex-1-ene. The zinc salt (or other suitable metal salt) of Formula 5 is then reacted with the reagent of Formula 6 where X represents a halogen, (bromine, chlorine or iodine) and B′ is defined similarly to B of Formula 1, except that B′ is a protected acid, ester, aldehyde, ketone or alcohol of the kind which is capable of withstanding the coupling reaction with the ethyne compound of Formula 4. The coupling reaction is conducted in the presence of a palladium complex catalyst having the formula $Pd(PQ_3)_4$ (Q is phenyl), or similar complex.

Alternatively, the ethyne compound of Formula 4 can be coupled with the reagent of Formula 6 in the presence of cuprous iodide, a suitable catalyst, typically of the formula $Pd(PQ_3)_2Cl_2$ (Q is phenyl) and an acid acceptor, such as triethylamine, by heating in a sealed tube under an inert gas (argon) atmosphere.

The reagent of Formula 6, that is a halogenated bicyclic aromatic or heteroaromatic compound, which contains the A-B′ group, as a hydrocarbon, ester, protected acid, alcohol, aldehyde or ketone, can be obtained in accordance with procedures known in the art. For the synthesis of the most preferred compounds of the present invention the reagent of Formula 6 is ethyl 6-bromo-2-naphthoate which can be obtained in accordance with the publication Anderson, L. C., J. Am. Chem. Soc. 1943, 65, 242).

Referring still to Reaction Scheme 1, the disubstituted ethyne compound of Formula 7 is treated with an epoxidizing reagent to yield the compounds of Formula 8. Generally speaking, the reaction of epoxidation is conducted in a secondary alcohol or ether type solvent such as iso-propyl alcohol or diethyl ether, under a protective blanket of inert gas, such as argon, at ambient temperature. Meta-chloroperoxybenzoic acid (MCPB) and magnesium monoperoxyphthalate acid (MMPP) serve as examples of preferred epoxidizing agents. The compounds of Formula 8, shown in Reaction Scheme 1, may already be the desired target compounds (that is compounds of Formula 1) or may be readily converted into the desired target compounds. This is indicated in Reaction Scheme 1 by conversion into "homologs and derivatives", by such steps as salt formation, esterification, desterification, amide formation and the like.

These steps relating to chemical transformations of the A-B group, which can be performed before or after epoxide formation, as applicable, are further discussed below.

Carboxylic acids are typically esterified by refluxing the acid in a solution of the appropriate alcohol in the presence of an acid catalyst such as sulfuric acid or thionyl chloride. Alternatively, the carboxylic acid can be condensed with the appropriate alcohol in the presence of dicyclohexylcarbodiimide and N,N-dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

A means for making compounds where A is $(CH_2)_n$ (n is 1–5) is to subject the compounds of Formula 1, (or of Formula 8) where B is an acid or other function, to homologation, using the well known Arndt-Eistert method of homologation, or other known homologation procedures.

Compounds of Formula 1, where A is an alkenyl group having one or more double bonds can be made for example, by having the requisite number of double bonds incorporated into the halogenated aryl or heteroaryl intermediate which is reacted with an ethyne compound of Formula 4. Generally speaking, such compounds where A is an unsaturated carbon chain can be obtained by synthetic schemes well known to the practicing organic chemist; for example by Wittig and like reactions, or by introduction of a double bond by elimination of halogen from an alpha-halo-carboxylic acid, ester or like carboxaldehyde. Compounds of Formula 1 where the A group has a triple (acetylenic) bond can be made by using the corresponding aryl or heteroaryl aldehyde intermediate. Such intermediate can be obtained by reactions well known in the art, for example, by reaction of a corresponding methyl ketone with strong base, such as lithium diisopropyl amide.

The acids and salts derived from compounds of Formula 1 and of Formula 8 are readily obtainable from the corresponding esters. Basic saponification with an alkali metal base will provide the acid. For example, an ester of Formula 1 or of Formula 8 may be dissolved in a polar solvent such as an alkanol, preferably under an inert atmosphere at room temperature, with about a three molar excess of base, for example, potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the acid is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethlaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Examples of substituted cyclohex-1-enyl ethyne reagents within the definition of Formula 4, which can be used to synthesize compounds of Formula 7 and after epoxidation the compounds of Formula 1 within the scope of the present invention are:
1-(2',6',6'-trimethylcyclohex-1'-enyl)ethyne;
1-(6',6'-dimethylcyclohex-1'-enyl)ethyne;
1-(3',3',6',6'-tetramethylcyclohex-1'-enyl)ethyne; and 1-(2',3',3',6',6'-pentamethylcyclohex-1'-enyl)ethyne.

Examples of halogenated bicyclic aromatic or heteroaromatic compounds within the definition of Formula 5, which can be used to synthesize compounds of Formula 7, by coupling with compounds of Formula 4, are:
ethyl 6-bromo-2-naphthoate
ethyl 6-bromoindene-3-carboxylate;
ethyl 6-bromobenzofuran-3-carboxylate;
ethyl 6-bromobenzothiophene-3-carboxylate;
ethyl 6-bromoquinoline-3-carboxylate;
ethyl 6-bromoisoquinoline-3-carboxylate.

Examples of compounds of Formula 1, other than the below described specific examples, which can be made in analogy to the below described specific examples, are:
ethyl 6-[2-(1,2-epoxy-2,6,6-trimethylcyclohexanyl)ethynyl]indene-3-carboxylate;
ethyl 6-[2-(1,2-epoxy-2,6,6-trimethylcyclohexanyl)ethynyl]benzofuran-3-carboxylate;
ethyl 6-[2-(1,2-epoxy-2,6,6-trimethylcyclohexanyl)ethynyl]benzothiophene-3-carboxylate;
ethyl 6-[2-(1,2-epoxy-2,6,6-trimethylcyclohexanyl)ethynyl]quinoline-3-carboxylate;
ethyl 6-[2-(1,2-epoxy-2,6,6-trimethylcyclohexanyl)ethynyl]isoquinoline-3-carboxylate;
ethyl 6-[2-(1,2-epoxy-6,6-dimethylcyclohexanyl)ethynyl]-2-naphthoate;
ethyl 6-[2-(1,2-epoxy-6,6-dimethylcyclohexanyl)ethynyl]indene-3-carboxylate;
ethyl 6-[2-(1,2-epoxy-6,6-dimethylcyclohexanyl)ethynyl]benzofuran-3-carboxylate;
ethyl 6-[2-(1,2-epoxy-6,6-dimethylcyclohexanyl)ethynyl]benzothiophene-3-carboxylate;
ethyl 6-[2-(1,2-epoxy-6,6-dimethylcyclohexanyl)ethynyl]quinoline-3-carboxylate;
ethyl 6-[2-(1,2-epoxy-6,6-dimethylcyclohexanyl)ethynyl]isoquinoline-3-carboxylate;
ethyl 6-[2-(1,2-epoxy-3,3,6,6,tetramethylcyclohexanyl)ethynyl]-2-naphthoate;
ethyl 6-[2-(1,2-epoxy-3,3,6,6,tetramethylcyclohexanyl)ethynyl]indene-3-carboxylate;
ethyl 6-[2-(1,2-epoxy-3,3,6,6,tetramethylcyclohexanyl)ethynyl]benzofuran-3-carboxylate;
ethyl 6-[2-(1,2-epoxy-3,3,6,6,tetramethylcyclohexanyl)ethynyl]benzothiophene-3-carboxylate;
ethyl 6-[2-(1,2-epoxy-3,3,6,6,tetramethylcyclohexanyl)ethynyl]quinoline-3-carboxylate;
ethyl 6-[2-(1,2-epoxy-3,3,6,6,tetramethylcyclohexanyl)ethynyl]isoquinoline-3-carboxylate;
ethyl 6-[2-(1,2-epoxy-2,3,3,6,6-pentamethylcyclohexanyl)-ethynyl]-2-naphthoate;
ethyl 6-[2-(1,2-epoxy-2,3,3,6,6-pentamethylcyclohexanyl)-ethynyl]indene-3-carboxylate;
ethyl 6-[2-(1,2-epoxy-2,3,3,6,6-pentamethylcyclohexanyl)ethynyl]benzofuran-3-carboxylate;
ethyl 6-[2-(1,2-epoxy-2,3,3,6,6-pentamethylcyclohexanyl)ethynyl]benzothiophene-3-carboxylate;
ethyl 6-[2-(1,2-epoxy-2,3,3,6,6-pentamethylcyclohexanyl)ethynyl]quinoline-3-carboxylate;
ethyl 6-[2-(1,2-epoxy-2,3,3,6,6-pentamethylcyclohexanyl)ethynyl]isoquinoline-3-carboxylate.

SPECIFIC EXAMPLES

Ethyl 6-[2-(2,6,6-trimethylcyclohex-1-enyl)ethynyl]-2-naphthoate (Compound 3)

To a solution of 0.503 g (3.3916 mmol) 1,3,3-trimethyl-2-ethynylcyclohexene (G. Kobrich et al. Chem Ber., 1966, 99,689.) in 4 ml of dry tetrahydrofuran at 0 degrees C. under argon was added dropwise 2.1 ml of 1.6M (3.36 mmol) of n-butyllithium in hexane. This mixture was stirred at 0 degrees C. for 10 minutes, at room temperature for 10 minutes and cooled again to 0 degrees C. To this was added, via cannula, a solution of 0.480 g (3.52 mmol) fused zinc chloride in 4 ml of tetrahydrofuran with stirring at 0 degrees C. for 40 minutes and at room temperature for 5 minutes. A solution of 0.9186 g (3.29 mmol) of ethyl 6-bromo-2-naphthoate (Anderson, L. C. J. Am. Chem. Soc., 1943, 65,242.) in 5 ml of dry tetrahydrofuran was transferred by cannula into a suspension of 0.410 g (0.3584 mmol) tetrakis(triphenylphosphine)palladium in 5 ml of dry tetrahydrofuran and stirred for 5 minutes at room temperature. This mixture was then treated via cannula with the solution of alkynyl zinc and the resultant mixture stirred at room temperature for 18 hours. Ice and 30 ml of 3N HCl was added and the products extracted with 4×50 ml ether. The combined ether extracts were washed with saturated NaHCO$_3$ and NaCl solution, dried (MgSO$_4$) and concentrated to give a brown oil. This oil was purified by HPLC (Waters 6000; Partisil M-9 10/50; 2% ethyl acetate in hexanes) to give the title compound as a yellow oil.

PMR (CDCl$_3$): 1.25(6H, S), 1.46(3H, t, J~7.5 Hz), 1.57(2H, m), 1.68(2H, m), 2.03(3H, s), 2.11(2H, m), 4.45(2H, q), 7.57(1H, dd, J~8.4 Hz, J~2.1 Hz), 7.82(1H, d, J~8.4 Hz), 7.88(1H, J~8.4 Hz), 7.96(1H, s), 8.07 (1H, dd, J~8.4 Hz, J~2.1 Hz), 8.56(1H, s).

6-[2-(2,6,6-trimethylcyclohex-1-enyl)ethynyl]-2-naphthoic acid (Compound 4)

To a stirred solution of 0.130 g (0.38 mmol) of ethyl-6-[2-(2,6,6-trimethylcyclohex-1-enyl)ethynyl]-2-naphthoate (Compound 3) in 0.7 ml of ethanol was added dropwise under nitrogen 0.9 ml of a 1.86M solution of KOH in ethanol and water. After being stirred at 50 degrees C. for 18 hours, solvent was removed in-vacuo and the residue treated with 1 ml of water and extracted with 1×3 ml portions of ether. The aqueous layer was then acidified with dilute HCl and extracted with 3×3 ml portions of ether. Combined ether extracts were dried (MgSO$_4$), filtered, and concentrated in-vacuo to give the title product.

PMR (CDCl$_3$): 1.22(6H, s), 1.55(2H, m), 1.66(2H, m), 2.01(3H, s), 2.10(2H, m), 7.69(1H, dd, J~8.4 Hz, J~1.5 Hz), 7.82(1H, d, J~8.4 Hz), 7.87(1H, d, J~8.4 Hz), 7.95(1H, s), 8.07(1H, dd, J~8.4 Hz, J~1.8 Hz), 8.58(1H, s).

(±)-6-[2-(1,2-Epoxy-2,6,6-trimethylcyclohexanyl)ethynyl]naphthoic acid (Compound 1)

To a suspension of 0.135 g (0.218 mmol) of 80% magnesium monoperoxyphthalate acid (MMPP) and 2 ml iso-propyl alcohol was added enough water (0.20 ml) to just dissolve the solid. This solution was added to a solution of 0.058 g (0.182 mmol) of 6-[2-(2,6,6-trimethylcyclohex-1-enyl)ethynyl]-2-naphthoic acid (Compound 4) in 1 ml iso-propyl alcohol and stirred at ambient temperature for 3 days. The solution was treated with 2 ml of brine and extracted with 3×10 ml ethyl acetate. The organic extracts were combined and washed with 5 ml saturated aqueous NaCl and dried (MgSO$_4$). The solvent was removed in-vacuo and the residue purified by flash chromatography (SiO$_2$, 75:25 ethyl acetate in hexanes) to give the title compound as a white solid PMR (CDCl$_3$): 1.16(1H,m), 1.24(3H,s), 1.28(3H,s), 1.40-1.52(3H,m), 1.58(3H,s), 1.83-1.94(2H,M), 7.56(1H,dd,J~8.5 Hz,J~1.3 Hz), 7.85(1H,d,J~8.7 Hz), 7.90(1H,J~8.5 Hz), 8.00(1H,s), 8.13 (1H,dd,J~8.7 Hz, J~1.3 Hz), 8.66(1H,s), 10.67 (1H,broad s).

What is claimed is:

1. A compound of the formula

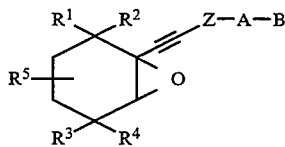

where R$_1$-R$_5$ are hydrogen, lower alkyl of 1-6 carbons, or halogen;

A is (CH$_2$)$_n$ where n is 0-5, lower branched chain alkyl having 3-6 carbons, cycloalkyl having 3-6 carbons, alkenyl having 2-6 carbons and 1 or 2 double bonds, alkynyl having 2-6 carbons and 1 or 2 triple bonds;

B is hydrogen, COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, or CR$_7$OR$_{13}$O, where R$_7$ is an alkyl, cycloalkyl or alkenyl group containing 1 to 5 carbons, R$_8$ is an alkyl group of 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5-10 carbons, or phenyl or lower alkylphenyl, R$_{11}$ is lower alkyl, phenyl or lower alkylphenyl, R$_{12}$ is lower alkyl, and R$_{13}$ is divalent alkyl radical of 2-5 carbons, and Z is selected from the groups:

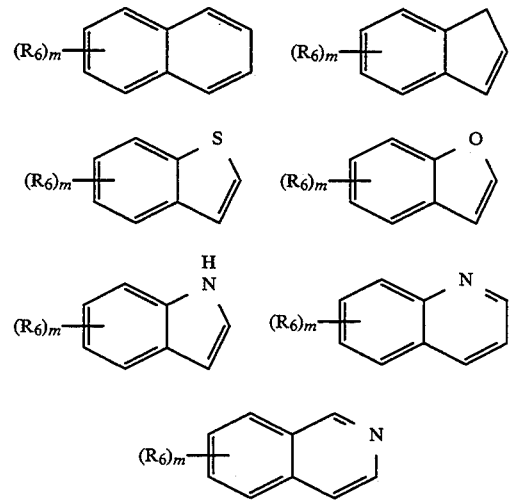

wherein R$_6$ is hydrogen, lower alkyl of 1-6 carbons, or halogen, R$_6$ can be attached to any available position on the Z group, and m is an integer between 0 to 4.

2. A compound of claim 1 wherein A is (CH$_2$)$_n$ and n is 0.

3. A compound of claim 1 wherein B is COOH or a pharmaceutically acceptable salt thereof, or B is COOR$_8$.

4. A compound of claim 1 where R$_1$ and R$_2$ are methyl.

5. A compound of claim 1 where R$_5$ is methyl.

6. A compound of claim 1 where Z is a naphthalene radical.

7. A compound of claim 1 where R$_3$ and R$_4$ are hydrogen.

8. A compound of claim 1 where the $R_5$ group is attached to the 2-position of the 1,2-epoxy cyclohexane nucleus.

9. A compound of claim 1 wherein Z is selected from a group consisting of divalent naphthalene, benzothiophene and benzofuran nucleus.

10. A pharmaceutical composition comprising a pharmaceutically acceptable excipient and one or more compounds set forth in claim 1 as the active ingredient.

11. A method for treating skin disorders in a mammal which method comprises administering alone or in conjunction with a pharmaceutically acceptable excipient a therapeutically effective amount of one or more compounds set forth in claim 1.

12. A method of claim 11 used for treating psoriasis in a mammal.

13. A compound of the formula

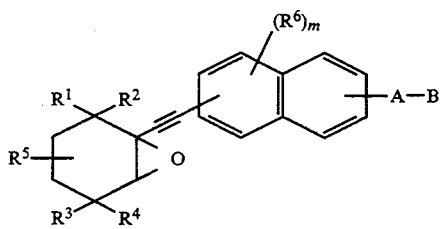

where $R_1$–$R_5$ are hydrogen, lower alkyl of 1–6 carbons, or halogen;
- A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;
- B is hydrogen, COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons;

$R_6$ is hydrogen, lower alkyl of 1–6 carbons, or halogen, and m is an integer between 0 to 4, or a pharmaceutically acceptable salt thereof.

14. A compound of claim 13 where the A-B group represents $(CH_2)_n$—COOH or pharmaceutically acceptable salt thereof, or $(CH_2)_n$—$COOR_8$ or $(CH_2)_n$—$CONR_9R_{10}$, and where n is 0, 1, or 2.

15. A compound of claim 13 where the $R_1$ and $R_2$ are methyl.

16. A compound of claim 13 where the $R_3$ and $R_4$ groups are hydrogen.

17. A compound of claim 13 where $R_5$ is methyl.

18. A compound of the formula

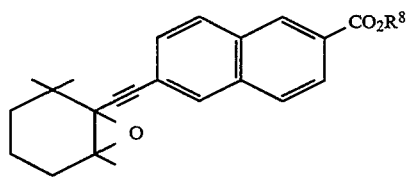

where $R_8$ is hydrogen or lower alkyl, or a pharmaceutically acceptable salt thereof.

19. The compound of claim 18 where $R_8$ is hydrogen, or a pharmaceutically acceptable salt thereof.

* * * * *